United States Patent
Chen et al.

(10) Patent No.: US 9,968,696 B2
(45) Date of Patent: May 15, 2018

(54) METHOD FOR STERILIZING MEMBRANE COMPRISING AN OXIDOREDUCTASE ENZYME AND ASSOCIATED BIOSENSOR

(71) Applicant: GENERAL ELECTRIC COMPANY, Schenectady, NY (US)

(72) Inventors: Rui Chen, Niskayuna, NY (US); Yida Xu, Shanghai (CN); Lin Chen, Shanghai (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 339 days.

(21) Appl. No.: 14/402,473

(22) PCT Filed: May 29, 2013

(86) PCT No.: PCT/SE2013/050616
§ 371 (c)(1),
(2) Date: Nov. 20, 2014

(87) PCT Pub. No.: WO2013/180634
PCT Pub. Date: Dec. 5, 2013

(65) Prior Publication Data
US 2015/0151013 A1 Jun. 4, 2015

(30) Foreign Application Priority Data

May 31, 2012 (CN) .......................... 2012 1 0177140

(51) Int. Cl.
| | | |
|---|---|---|
| C12N 9/00 | (2006.01) | |
| A61L 2/08 | (2006.01) | |
| C12Q 1/26 | (2006.01) | |
| C12Q 1/00 | (2006.01) | |
| C12Q 1/54 | (2006.01) | |
| A61L 2/00 | (2006.01) | |

(52) U.S. Cl.
CPC .............. *A61L 2/081* (2013.01); *C12Q 1/005* (2013.01); *C12Q 1/006* (2013.01); *C12Q 1/26* (2013.01); *C12Q 1/54* (2013.01); *A61L 2/0035* (2013.01); *G01N 2333/904* (2013.01)

(58) Field of Classification Search
CPC . A61L 2/081; A61L 2/0035; G01N 2333/904; G01N 2333/902; C12C 1/26
See application file for complete search history.

(56) References Cited

U.S. PATENT DOCUMENTS

| | | |
|---|---|---|
| 7,848,487 B2 | 12/2010 | Miekka et al. |
| 2004/0120848 A1 | 6/2004 | Teodorczyk |
| 2009/0166178 A1 | 7/2009 | Harmon et al. |
| 2010/0293892 A1* | 11/2010 | Curry ................. A61B 5/14532 53/403 |

FOREIGN PATENT DOCUMENTS

| | | |
|---|---|---|
| WO | 2007022485 | 2/2007 |
| WO | 2009126942 | 10/2009 |
| WO | 2010068587 | 6/2010 |

OTHER PUBLICATIONS

Search Report issued in EP Application No. 13796861.6 (dated Jan. 26, 2016).
Von Woedtke et al. "Sterilization of enzyme glucose sensors: problems and concepts", Biosensors & Bioelectronics, 17:373-382 (2002).
PCT/SE2013/050616 ISRWO dated Sep. 10, 2013.

* cited by examiner

*Primary Examiner* — Kara Johnson
(74) *Attorney, Agent, or Firm* — Wood IP LLC

(57) ABSTRACT

A method for sterilizing a membrane comprising an oxidoreductase enzyme in an environment having a relative humidity, comprises: irradiating the membrane comprising an oxidoreductase enzyme with gamma radiation under vacuum at a relative humidity lower than the relative humidity of the environment. Associated biosensors are also described.

13 Claims, 2 Drawing Sheets

METHOD FOR STERILIZING MEMBRANE COMPRISING AN OXIDOREDUCTASE ENZYME AND ASSOCIATED BIOSENSOR

This application is a filing under 35 U.S.C. 371 of international application number PCT/SE2013/050616, filed May 29, 2013, which claims priority to China application number 201210177140.7 filed May 31, 2012, the entire disclosure of which is hereby incorporated by reference.

BACKGROUND

The invention relates generally to methods for sterilizing membranes comprising oxidoreductase enzymes such as glucose oxidase and associated biosensors.

Biosensors comprising membranes comprising glucose oxidase are used for continuous and/or automatic monitoring of glucose in bodily fluid such as in the blood stream or in interstitial fluid of certain individuals such as those with diabetes. Biosensors comprising membranes comprising the oxidoreductases glucose oxidase, lactate oxidase and glutamate oxidase are also used to automatically and/or continually detect the level of glucose, lactate and glutamate respectively in bioreactors to monitor the cell growth.

It is important that the biosensors to be sterile to prevent at least potential damages from biological contaminant or pathogen (bacteria, fungi and viruses etc.) to the health and safety of the user or to the normal operation of the bioreactor.

Gamma irradiation, autoclave treatment, and ethylene oxide treatment, are some of the techniques for sterilization. However, besides eliminating/inactivating the unwanted and potentially dangerous biological contaminant or pathogen, the gamma radiation also damages the membranes comprising glucose oxidase and decreases the sensitivity of the biosensors. Therefore, methods have been developed to protect the biosensor and/or the membrane comprising glucose oxidase while sterilizing the biosensor and/or the membrane comprising glucose oxidase.

For example, US Patent Application Publication No. 2010/0293892 discloses a method of packaging an enzyme (glucose oxidase) sensor that prevents damage to the enzyme sensor and that maintains the sterility of the enzyme sensor by inflating the package with excess pressure of an inert gas or drawing a vacuum on the package before sealing the package and exposing the sealed package to radiation.

It is found that by using the currently available methods, such as those proposed in the patent application mentioned above, to sterilize the biosensor and/or the membrane comprising oxidoreductases by gamma irradiation, the loss of sensitivity of the biosensor is too high in certain application environments.

Therefore, there is a need to develop a new method for sterilizing the biosensor and/or the membrane comprising oxidoreductases.

BRIEF DESCRIPTION

In one example, a method for sterilizing a membrane comprising an oxidoreductase enzyme in an environment having a relative humidity is provided, comprising: irradiating the membrane comprising an oxidoreductase enzyme with gamma radiation under vacuum at a relative humidity lower than the relative humidity of the environment.

In another example, a biosensor is provided. The biosensor comprises the membrane comprising an oxidoreductase enzyme sterilized using the method described above.

In yet another example, a biosensor comprising a membrane comprising an oxidoreductase enzyme is provided. The biosensor is sterilized in an environment having a relative humidity by: irradiating with gamma radiation while the membrane comprising an oxidoreductase enzyme is under vacuum at a relative humidity lower than the relative humidity of the environment.

These and other advantages and features will be better understood from the following detailed description of embodiments of the invention that is provided in connection with the accompanying drawings.

DETAILED DESCRIPTION

Figure 1:
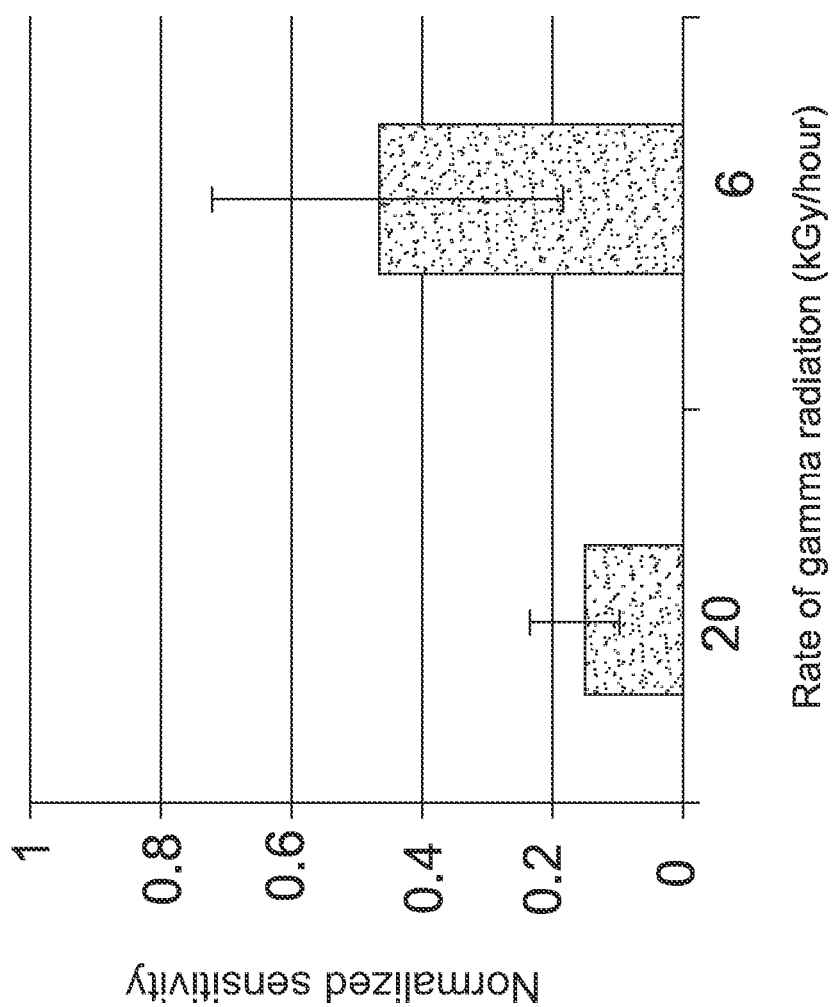
FIG. 1 is a diagram obtained in example 1.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

Any numerical value ranges recited herein include all values from the lower value to the upper value in increments of one unit provided that there is a separation of at least 2 units between any lower value and corresponding higher value. As an example, if it is stated that the amount of a component or a value of a process variable such as, for example, temperature, pressure, rate, time and the like is, for example, from 25 to 40, it is intended that values such as 30 to 35, 26 to 39, 33 to 35, 28 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

In the following specification and claims, the singular forms "a", "an" and "the" include plural referents, unless the context clearly dictates otherwise. Moreover, the suffix "(s)" as used herein is usually intended to include both the singular and the plural of the term that it modifies, thereby including one or more of that term.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. For example, in some circumstances, an event or capacity may be expected, while in other circumstances, the event or capacity may not occur. This distinction is captured by the terms "may" and "may be".

As used herein, the terms "sterilize", "sterilizing", "sterilization" and terms of like indicate a reduction in the level of at least one active biological contaminant or pathogen found in the membrane comprising an oxidoreductase enzyme and/or the biosensor being treated according to the present invention.

As used herein, the term "biological contaminant or pathogen" indicates a biological contaminant or pathogen that, upon direct or indirect contact with the membrane comprising an oxidoreductase enzyme and/or the biosensor, may have a deleterious effect on the membrane comprising an oxidoreductase enzyme or upon a recipient thereof. Such biological contaminants or pathogens include various bacteria, fungi and viruses etc.

As used herein, the term "active biological contaminant or pathogen" indicates a biological contaminant or pathogen that is capable of causing a deleterious effect, either alone or in combination with another factor, such as a second biological contaminant or pathogen or a native protein (wild-type or mutant) or antibody, in the membrane comprising an oxidoreductase enzyme and/or a recipient thereof.

In one aspect the invention discloses a method for sterilizing a membrane comprising an oxidoreductase enzyme comprising the steps of: a) providing a receptacle containing a desiccant and a membrane comprising an oxidoreductase enzyme; b) evacuating the receptacle and c) irradiating the evacuated receptacle containing the desiccant and the membrane comprising an oxidoreductase enzyme with gamma radiation. The receptacle may e.g. be a flexible bag, such as a plastic bag or a laminate bag and the method may also involve a step between step b) and step c), where the receptacle or bag is sealed, e.g. by heat-sealing. The evacuation in step b) may be accomplished by subjecting the interior of the receptacle to a pressure lower than atmospheric pressure, such as a pressure lower than 50 kPa or lower than 25 kPa. This can be done e.g. by applying a vacuum to the receptacle.

The oxidoreductase enzyme may be selected from the group consisting of glucose oxidase, lactate oxidase and glutamate oxidase. Membranes comprising these enzymes can be used to determine concentrations of glucose, lactate and glutamate in e.g. bioreactors.

In some embodiments, the recipient may be the bioreactor in which the biosensor works and the cell grows. If the biosensor is not sterilized, the "biological contaminant or pathogen" on the biosensor and/or the membrane comprising an oxidoreductase enzyme may cause the contamination of cell culture inside the bioreactor and the failure of the desired cell culture.

The membrane comprising an oxidoreductase enzyme may be any membrane that comprises an oxidoreductase enzyme, such as glucose oxidase. In some embodiments, the membrane comprising an oxidoreductase enzyme is any membrane comprising an oxidoreductase enzyme that may be used in a biosensor, e.g., for the detection of the level of glucose, lactate or glutamate. Such membranes are commercially available from, e.g., NOVA Biomedical Corporation company, Waltham, Mass., USA, YSI Incorporated and Xylem, Inc., Yellow Springs, Ohio, USA and Biology Institute of Shandong Academy of Science, Jinan, Shandong, China.

In some embodiments, the biosensor for the detection of the level of glucose, lactate or glutamate comprises a combination electrode and a membrane comprising an oxidoreductase enzyme. The combination electrode comprises two electrodes and an insulator between the electrodes. The electrodes may be made of, for example, platinum (Pt) and/or Ag/AgCl. The membrane comprising an oxidoreductase enzyme may be assembled to the biosensor after or before sterilization. In the latter case, the biosensor is sterilized in an environment having a relative humidity by: irradiating with gamma radiation while the membrane comprising an oxidoreductase enzyme is under vacuum at a relative humidity lower than the relative humidity of the environment.

Gamma radiation may be produced by isotopes of cobalt or cesium. According to examples of the methods of the invention, the gamma radiation may be applied at a rate effective for the sterilization of the membrane comprising an oxidoreductase enzyme and/or the biosensor, while not causing an unacceptable level of damage to the membrane comprising an oxidoreductase enzyme. Suitable rates of gamma radiation may vary depending upon certain features of examples of the methods of the invention being employed, such as the nature and characteristics of the particular membrane comprising an oxidoreductase enzyme and/or the biosensor being irradiated, and/or the particular biological contaminants or pathogens being inactivated. Preferably, the rate of gamma radiation is constant for the duration of the sterilization procedure. When this is impractical or otherwise not desired, a variable or discontinuous irradiation may be utilized.

According to examples of the methods of the invention, the rate of gamma radiation may be optimized depending, for example, on the biological materials used. Both low ($\leq 3$ kGy/hour) and high ($>3$ kGy/hour) rates may be utilized in the methods to achieve the desired results. Although reducing the rate of gamma radiation may serve to decrease damage to the membrane comprising an oxidoreductase enzyme, it will also result in longer irradiation times normally required to achieve a particular desired total dose. A higher dose rate may therefore be preferred in certain circumstances, such as to minimize logistical issues and costs, and may be possible when used in accordance with the methods for protecting a membrane comprising an oxidoreductase enzyme from irradiation. According to one embodiment of the invention, the rate of gamma radiation is about 20 kGy/hour.

According to examples of the methods of the invention, irradiating with the gamma radiation is applied for a time period that is effective to sterilize the membrane comprising an oxidoreductase enzyme and/or the biosensor. Combined with the radiation rate, the appropriate irradiation time results in the appropriate dose of irradiation being applied to the membrane comprising an oxidoreductase enzyme and/or the biosensor. Suitable irradiation times may vary depending upon the particular rate of radiation involved and/or the nature and characteristics of the particular membrane comprising an oxidoreductase enzyme and/or the biosensor being irradiated.

According to examples of the methods of the invention, the time and rate of irradiating with gamma radiation will depend on the total dose effective to sterilize the membrane comprising an oxidoreductase enzyme and/or the biosensor, while not producing an unacceptable level of damage to that membrane comprising an oxidoreductase enzyme. Suitable total doses of gamma radiation may vary depending upon certain features of examples of the methods of the invention being employed, such as the nature and characteristics of the particular membrane comprising an oxidoreductase enzyme and/or the biosensor being irradiated, the particular form of gamma radiation involved and/or the particular biological contaminants or pathogens being inactivated. In one example, the total dose of gamma radiation is at least about 25 kGy, and in other examples it may be in a range of from about 25 kGy to about 40 kGy.

According to examples of the methods of the invention, irradiating with gamma radiation may occur at any temperature that is not deleterious to the membrane comprising an oxidoreductase enzyme and/or the biosensor being sterilized. The irradiation occurs at any temperature that does not substantially damage the membrane comprising an oxidoreductase enzyme and/or the biosensor.

In some embodiments, irradiating with gamma radiation is at an ambient temperature. According to another embodiment, the irradiation is at a reduced temperature, e.g., a temperature below ambient temperature, such as 0° C., −20° C., −40° C., −60° C., −78° C. or −196° C. According to another embodiment, the irradiation is at elevated temperature, e.g., a temperature above ambient temperature, such as 37° C., 60° C., 72° C. or 80° C.

In certain embodiments, the temperature at which irradiation is performed may be found to lie within a range, rather than at a specific point.

According to examples of the methods of the invention, the irradiation may occur at any pressure which is not deleterious to the membrane comprising an oxidoreductase enzyme and/or the biosensor being sterilized. According to one embodiment, the irradiation is at an ambient pressure.

Vacuum may be realized in many ways. In some embodiments, the membrane comprising an oxidoreductase enzyme or the biosensor comprising the membrane comprising an oxidoreductase enzyme may be put in a package which is then drawn vacuum.

As used herein, the term "relative humidity" indicates the amount of water vapor in a mixture of air and water vapor, i.e., the ratio of the partial pressure of water vapor in the air-water mixture to the saturated vapor pressure of water at the prescribed temperature. In some embodiments, the relative humidity is detected using a hygrothermograph.

In some embodiments, both the membrane comprising an oxidoreductase enzyme or the biosensor comprising a membrane comprising an oxidoreductase enzyme and a desiccant are placed in a vacuum package so that the membrane comprising an oxidoreductase enzyme is held under vacuum with a relative humidity lower than, or e.g., about half of, the relative humidity of the environment. Examples of a desiccant material include, but are not limited to silica gel, activated charcoal, calcium sulfate, calcium chloride, montmorillonite clay, and molecular sieves. Different desiccant materials may result in different relative humidity in a particular package.

As can be seen from the following examples, it is surprisingly found that the sensitivity of the biosensor comprising a membrane comprising an oxidoreductase enzyme held under vacuum with a relative humidity lower than a relative humidity of the environment while being irradiated with gamma radiation is significantly higher than the sensitivity of the biosensor comprising a membrane comprising an oxidoreductase enzyme held under vacuum with a relative humidity equal to a relative humidity of the environment while being irradiated with gamma radiation.

The invention also discloses a bioreactor equipped with at least one biosensor comprising a membrane comprising an oxidoreductase enzyme as described above. The bioreactor may e.g. comprise a presterilized plastic bag as the bioreactor vessel and the presterilized plastic bag may comprise the sterilized biosensor(s) described above. Such a bioreactor is useful for monitoring glucose, lactate, glutamate and/or other nutrients and metabolites during cell cultivation.

EXAMPLES

The following examples are included to provide additional guidance to those of ordinary skill in the art in practicing the claimed invention. These examples do not limit the invention of the appended claims.

The membranes comprising glucose oxidase and dry-sealed in an aluminum foil pouch were obtained from NOVA Biomedical Corporation company, Waltham, Mass., USA and were stored at 4° C. before use. In the following examples, unless otherwise noted, all irradiation was accomplished using a $^{60}$Co source at an ambient temperature and pressure, and dosages of gamma radiations were in a range of from about 25 kGy to about 40 kGy.

Example 1

Four membranes comprising glucose oxidase were sterilized by being irradiated with gamma radiation in the aluminum foil pouches. The rate of gamma radiation for two of the four membranes comprising glucose oxidase was 6 kGy/hour. The rate of gamma radiation for the other two of the four membranes comprising glucose oxidase was 20 kGy/hour.

Each of the four membranes comprising glucose oxidase was assembled to a combination electrode comprising a Pt working electrode, an Ag/AgCl reference/counter electrode and an insulator between the Pt working electrode and the Ag/AgCl reference/counter electrode to obtain a biosensor.

A pack of phosphate buffer saline (PBS) buffer powders for a bioanalyzer (SBA-40C, Biology Institute of Shandong Academy of Science, Jinan, Shandong, China) was obtained from the Biology Institute of Shandong Academy of Science, Shandong, China and was dissolved using 500 ml deionized water to obtain a PBS buffer solution. Each of the biosensors was soaked in the phosphate buffered saline (PBS) buffer solution comprising glucose, and connected to a potentiostat via cables. A voltage of 0.6 V was applied to the biosensor using the potentiostat.

The concentration of the glucose in the PBS buffer solution was increased step by step and the current was read from the potentiostat at each concentration. A two dimensional figure was made using the concentration of the glucose as the horizontal axis and the corresponding current as the vertical axis. The slope of the figure of the current vs. the concentration of glucose was obtained and used to stand for the sensitivity of the bio sensor.

The sensitivities obtained above were respectively divided by the sensitivities of biosensors comprising membranes comprising glucose oxidase without gamma irradiation to yield values of normalized sensitivities shown in FIG. 1. It can be seen from FIG. 1 that about 50% of the sensitivity remained after 25-40 kGy gamma irradiation at 6 kGy/hour, but only less than 20% of the sensitivity remained after 25-40 kGy gamma irradiation at 20 kGy/hour.

Example 2

Each of two membranes comprising glucose oxidase was put together with 3 packs of silica gel desiccants in one plastic pack to decrease the relative humidity in the plastic pack to about 26% while the relative humidity of the environment was about 45% to about 60%. Each of two membranes comprising glucose oxidase was put in one plastic pack while the relative humidity of the environment was about 45% to about 60%. All of the four plastic packs were vacuumed for about 1 minute before being heat-sealed and were irradiated with about 25 kGy to about 40 kGy gamma radiation at a dose rate of about 20 kGy/hour.

Figure 2:
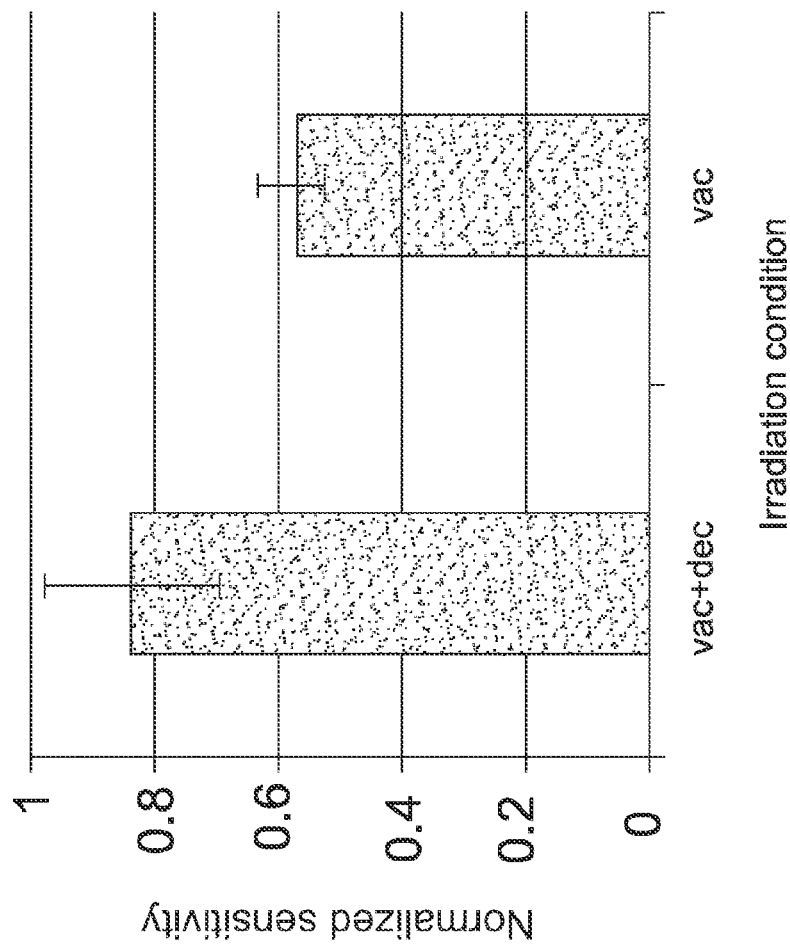
FIG. 2 is a diagram obtained in example 2.

The sensitivities of the biosensors were obtained in the same ways as in example 1 above and were respectively divided by the sensitivities of biosensors comprising membranes without gamma irradiation to yield values of normalized sensitivities shown in FIG. 2.

It can be seen from FIG. 2 that when the membranes comprising glucose oxidase were held under vacuum with a relative humidity of about 26%, after gamma irradiation, about 85% of the sensitivity remained. When the membranes comprising glucose oxidase were held under vacuum with a relative humidity of the environment, i.e., about 45% to about 60%, after gamma irradiation, less than 60% of sensitivity remained.

While the methods have been illustrated and described in typical embodiments, these are not intended to be limited to the details shown, since various modifications and substitutions may be made without departing in any way from the spirit of the disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method for sterilizing a membrane comprising an oxidoreductase enzyme (MCOE), the method comprising:
   a) providing a receptacle containing a desiccant and the MCOE;
   b) applying vacuum to the receptacle containing the desiccant and the MCOE such that the interior pressure of the receptacle is lower than atmospheric pressure;
   c) sealing the vacuumed receptacle containing the desiccant and the MCOE; and
   d) irradiating the vacuumed receptacle containing the desiccant and the MCOE with gamma radiation.

2. The method of claim 1, wherein the receptacle is a flexible bag.

3. The method of claim 1, wherein the interior pressure of the receptacle is 50 kPa lower than atmospheric pressure.

4. The method of claim 1, wherein the desiccant comprises silica gel, activated charcoal, calcium sulfate, calcium chloride, montmorillonite clay, and/or a molecular sieve.

5. The method of claim 1, wherein the rate of the gamma radiation is about 20 kGy/hour.

6. The method of claim 1, wherein the dosage of the gamma radiation is in a range of from about 25 kGy to about 40 kGy.

7. The method of claim 1, wherein the oxidoreductase enzyme is selected from the group consisting of glucose oxidase, lactate oxidase and glutamate oxidase.

8. The method of claim 1, wherein the oxidoreductase enzyme is glucose oxidase.

9. The method of claim 1, wherein the membrane comprising an oxidoreductase enzyme is in a biosensor.

10. A method for sterilizing a membrane comprising an oxidoreductase enzyme (MCOE) contained in a receptacle, wherein the receptacle has an environment having a relative humidity, the method comprising:
    a) lowering the relative humidity inside the receptacle by adding a desiccant to the receptacle containing the MCOE;
    b) applying a vacuum to the receptacle containing the desiccant and the MCOE of step a);
    c) maintaining the receptacle containing the desiccant and the MCOE under vacuum;
    d) sealing the receptacle containing the desiccant and the MCOE; and
    e) irradiating the vacuumed receptacle containing the desiccant and the MCOE with gamma radiation.

11. The method of claim 10, wherein the membrane comprising an oxidoreductase enzyme is held under vacuum with the relative humidity of about half of the relative humidity of the environment.

12. The method of claim 10, further comprising a step of sealing the receptacle between a) and b).

13. The method of claim 10, wherein the desiccant comprises silica gel, activated charcoal, calcium sulfate, calcium chloride, montmorillonite clay, and/or a molecular sieve.

* * * * *